United States Patent [19]

Lam et al.

[11] Patent Number: 5,104,407
[45] Date of Patent: Apr. 14, 1992

[54] SELECTIVELY FLEXIBLE ANNULOPLASTY RING

[75] Inventors: Hung L. Lam, Norco; Than Nguyen, Huntington Beach, both of Calif.; Alain Carpentier, Paris, France

[73] Assignee: Baxter International Inc., Deerfield, Ill.

[21] Appl. No.: 587,486

[22] Filed: Sep. 20, 1990

Related U.S. Application Data

[63] Continuation of Ser. No. 310,424, Feb. 13, 1989, abandoned.

[51] Int. Cl.⁵ .................................. A61F 2/24
[52] U.S. Cl. ............................................ 623/2
[58] Field of Search ............................ 623/2

[56] References Cited

U.S. PATENT DOCUMENTS

| | | |
|---|---|---|
| 3,656,185 | 4/1972 | Carpentier . |
| 4,042,979 | 7/1977 | Angell . |
| 4,055,861 | 11/1977 | Carpentier et al. . |
| 4,164,046 | 7/1979 | Cooley . |
| 4,204,283 | 5/1980 | Bellhouse et al. . |
| 4,290,151 | 9/1981 | Massana . |
| 4,306,319 | 12/1981 | Kaster . |
| 4,489,446 | 12/1984 | Reed . |
| 4,602,911 | 7/1986 | Ahmadi et al. . |

FOREIGN PATENT DOCUMENTS 0257874  3/1988  European Pat. Off. .

OTHER PUBLICATIONS

"Clinical and Hemodynamic Performance of a Totally Flexible Prosthetic Ring for Atrioventricular Valve Reconstruction", Duran, Ubago; The Annals of Thoracic Surgery; vol. 22, No. 5; pp. 458–463.

"Conservative Surgery of the Mitral Valve. Annuloplasty on a New Adjustable Ring"; Massana, Calbet and Castells; Cardio. Surg., 1980.

Primary Examiner—David J. Isabella
Assistant Examiner—Stephanie L. Iantorno
Attorney, Agent, or Firm—Michael C. Schiffer

[57] ABSTRACT

An annuloplasty ring prosthesis which is formed from a selectively flexible body element having at least one defined length about its circumference which is substantially rigid. The remainder of the body element gradually increases in flexibility. The body element is a substantially annular shaped body element which is designed to be sutured to the annulus of a heart valve. The body element is formed from a non-corrosive, anti-magnetic material, and is wrapped in a material through which sutures can be drawn to suture the prosthesis to the heart valve annulus.

49 Claims, 3 Drawing Sheets

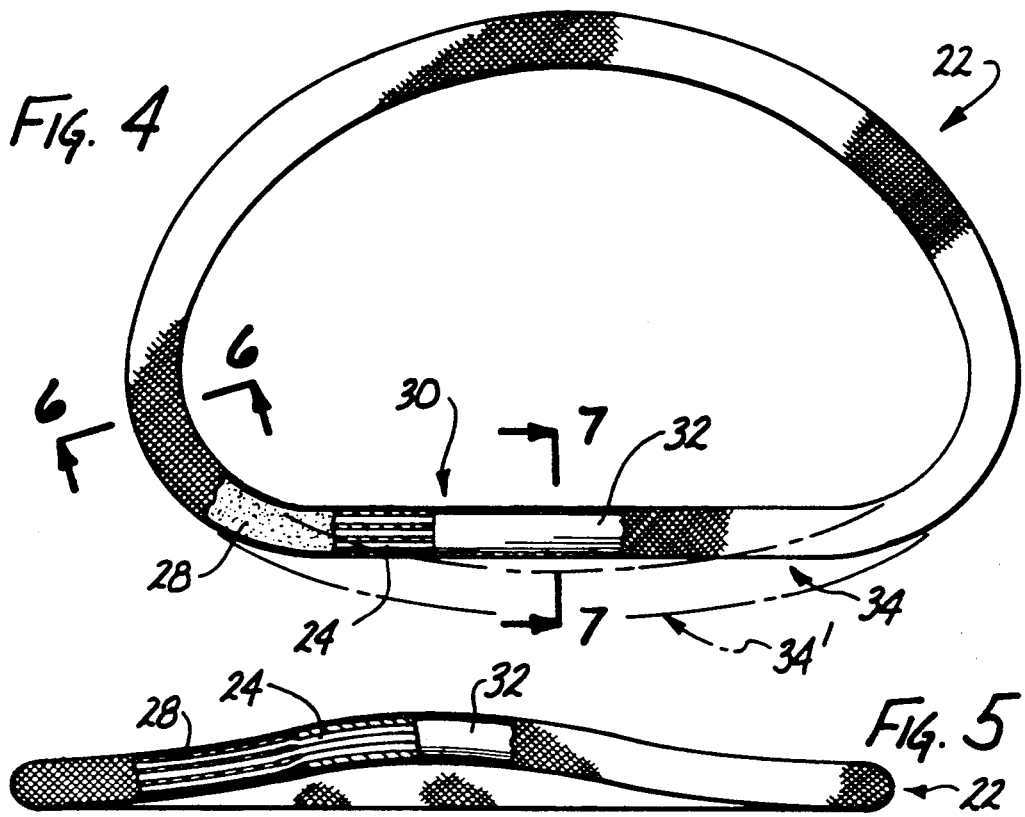
Fig. 4
Fig. 5
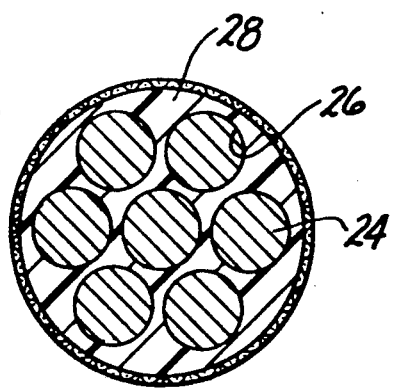
Fig. 6
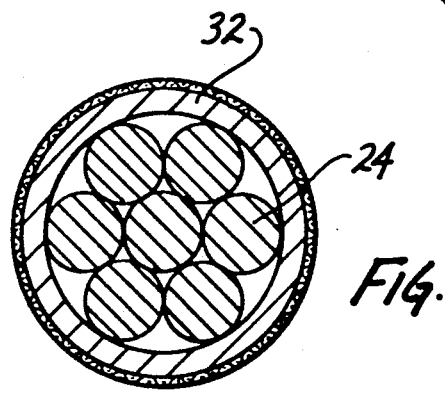
Fig. 7
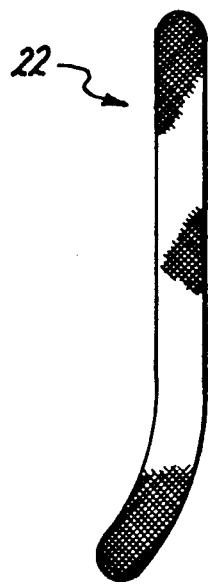
Fig. 3

SELECTIVELY FLEXIBLE ANNULOPLASTY RING

This is a continuation, of application Ser. No. 07/310,424 filed on Feb. 13, 1989 now abandoned.

BACKGROUND OF THE INVENTION

The present invention relates to a support for a natural human heart which may be used for the surgical correction of a deformed heart valve, specifically a heart valve which has become dilated. In particular, the present invention relates to an annuloplasty ring prosthesis for implantation about heart valves.

The human heart generally includes four valves. Of these valves the more critical ones are known as the mitral valve, which is located in the left atrioventricular opening, and the tricuspid valve, which is located in the right atrioventricular opening. Both of these valves are intended to prevent regurgitation of blood from the ventricle into the atrium when the ventricle contracts. In preventing blood regurgitation both valves must be able to withstand considerable back pressure as the ventricle contracts. The valve cusps are anchored to the muscular wall of the heart by delicate but strong fibrous cords in order to support the cusps during ventricular contraction. Furthermore, the geometry of the heart valves ensure that the cusps over lay each other to assist in controlling the regurgitation of the blood during ventricular contraction.

Diseases and certain natural defects to heart valves can impair the functioning of the cusps in preventing regurgitation. For example, certain diseases cause the dilation of the heart valve annulus. Dilation may also cause deformation of the valve geometry or shape displacing one or more of the valve cusps from the center of the valve. Other diseases or natural heart valve defects result in deformation of the valve annulus with little or no dilation. Dilation and/or deformation result in the displacement of the cusps away from the center of the valve. This results in an ineffective closure of the valve during ventricular contraction, which results in the regurgitation or leakage of blood during ventricle contraction. For example, diseases such as rheumatic fever or bacterial inflammations of the heart tissue can cause distortion or dilation of the valvular annulus. Other diseases or malformations result in the distortion of the cusps, which will also lead to ineffective closure of the valve.

One method of repairing an impaired valve is to completely replace the valve. This method is particularly suitable for replacing a heart valve when one of the cusps has been severely damaged or deformed. However, presently available artificial heart valves are not as durable as natural heart valves, and it is usually more preferable if the patient's heart valve can be left intact.

While it is difficult to retain a heart having diseased or deformed cusps, the ability to surgically correct the deformation of the valve annulus at least provides the possibility of retaining the patient's valve intact. That is, while the replacement of the entire valve eliminates the immediate problem associated with a dilated valve annulus, presently available heart valves do not possess the same durability as natural heart valves. It is thus desirable to save the valve instead of performing a complete replacement.

Techniques have been developed to repair the shape of the dilated or elongated valve. These techniques, known as annuloplasty, is a surgical procedure of restricting the dilation of the valve annulus. Typically, a prosthesis is sutured about the base of the valve leaflets to restrict the dilation of the valve annulus. The prosthesis restricts the movement of the valve annulus during the opening and closing of the valve. The general desire in designing a prosthesis is to provide sufficient rigidity to ensure an adequate support of the valve annulus to allow for the possible healing of the valve annulus, while allowing for as close as possible the natural movement of the valve annulus during the opening and closing of the valve. This is particularly important since such prostheses are not normally removed from the heart valve, even if the valve annulus heals to a normal geometry.

Over the years different types of prostheses have been developed for use in annuloplasty surgery. In general prostheses are annular or partially annular shaped members which fit about the base of the valve annulus against the leaflets. Initially the prostheses were designed as rigid frame members, to correct the dilation and reshape the valve annulus to the natural state. These annular prostheses were formed from a metallic or other rigid material, which flexes little, if at all, during the normal opening and closing of the valve. Examples of rigid annuloplasty ring prostheses are disclosed in U.S. Pat. Nos. 3,656,185, issued to Carpentier on Apr. 18, 1972; and 4,164,046, issued to Cooley on Aug. 14, 1979. Certain artificial heart valves have also been developed with rigid frame members similar to the rigidity of the described valve prosthesis. An example of this type of heart valve are disclosed in U.S. Pat. Nos. 4,204,283, issued to Bellhouse et al on May 27, 1980; and 4,306,319, issued to Kaster on Dec. 22, 1981.

As stated, rigid annuloplasty ring prostheses adequately promote the healing of the valve annulus by restricting valve dilation and reshaping the valve annulus. However, this rigidity prevents the normal flexibility of the valve annulus. That is, a normal heart valve annulus continuously flexes during the cardiac cycle, and a rigid ring prosthesis interferes with this movement. Since it is standard to retain the prosthesis, even after the valve annulus has healed, the rigidity of the prothesis will permanently impair the functioning of the valve and the associated ventricle. Another disadvantage with a rigid ring prosthesis is the tendency for the sutures to become torn loose during the normal movement of the valve annulus.

Other workers have suggested the use of completely flexible annuloplasty ring prostheses, in order to overcome the disadvantages of rigid ring prostheses. This type of prosthesis is formed with a cloth or other very flexible material frame member. The resulting prosthesis provides little, if any resistance to the dilation of the annulus during the opening and closing of the valve. Furthermore, while these types of annuloplasty ring prothesis offer increased flexibility, such prosthesis fail to correct that valve disfunction due to the deformation of the valve annulus.

A further disadvantage with completely flexible ring prostheses is that the circumference of the ring is not fixed. That is, as the prothesis is being sutured to the annulus using, what are known as mattress sutures, the body of the prosthesis may become bunched at localized areas. This bunching of the prosthesis is generally referred to as multiple plications of the ring prosthesis. The resulting sutured prosthesis will not provide the desired reshaping of the valve annulus.

Examples of completely flexible ring prostheses are disclosed in U.S. Pat. No. 4,290,151, issued to Massana on Sept. 22, 1981, and are discussed in the articles of Carlos D. Duran and Jose Luis M. Ubago, "Clinical and Hemodymanic Performance of a Totally Flexible Prosthetic Ring for Atrioventricular Valve Reconstruction", 5 Annals of Thoracic Surgery, (No. 5), 458–463, (November 1976) and M. Puig Massana et al, "Conservative Surgery of the Mitral Valve Annuloplasty on a New Adjustable Ring", Cardiovascular Surgery 1980, 30–37, (1981).

Still further types of annuloplasty ring prostheses are designed to allow for adjustment of the ring circumference, either during the surgical implantation, or as the ring prosthesis during the opening and closing of the valve. This type of adjustable prosthesis is typically designed in combination with a rigid, or at least partially rigid frame member. For example, the ring prosthesis taught in U.S. Pat. No. 4,489,446, issued to Reed on Dec. 25, 1984, allows for self adjustment of the prosthesis annulus by constructing the valve frame member in two reciprocating pieces. However, while the resulting prosthesis is adjustable in at least one direction, the individual frame members are formed from a rigid material and thus the prosthesis suffers the same disadvantages with the rigid ring prosthesis discussed above.

Other examples of adjustable ring prostheses are taught in U.S. Pat. No. 4,602,911, issued to Ahmadi et al and 4,042,979, issued to Angell on Aug. 23, 1977, provide for mechanism of adjusting the ring circumference. In Ahmadi et al the ring prosthesis frame is a coiled spring ribbon which is adjusted by a mechanical screw assembly. In Angell, a drawstring is used to adjust the circumference of a rigid frame member. Again, these ring prostheses suffer from the disadvantages of the rigid ring prosthesis discussed above. The Angell prosthesis could also possess a substantially flexible portion after suturing which could include multiple plications for the reasons discussed above for the completely flexible prosthesis.

A further disadvantage with the Angell prosthesis relates to the design of the adjusting mechanism. The Angell prosthesis includes a rigid partial annular member. The open end of this member forms a gap which can be narrowed by tightening the drawstring. The tighter the drawstring is pulled the narrower the gap. The stress applied to the ring prostheses during the opening and closing of the valve is primarily directed to the drawstring. Thus failure of the drawstring allows the prosthesis annulus to expand, allowing the valve to dilate.

It would thus be advantageous to design an annuloplasty ring prosthesis having selective flexibility more closely resembling the naturally flexibility of the valve annulus to allow for a more natural movement of the valve during the cardiac cycle, while possessing selected areas of rigidity to allow for the reshaping of the valve. This annuloplasty ring prosthesis should also be formed from a substantially stiff body element to minimize the potential of forming multiple plications about the circumference of the prosthesis during the suturing procedure.

An annuloplasty ring prosthesis which partially achieved these results was taught in U.S. Pat. No. 4,055,861, issued to Carpentier on Nov. 1, 1977. The support taught and disclosed is described as being deformable, to an equal degree and simultaneously in all directions within and outside its resting plane, so as to form a skew curve. The preferred support is described as having the elasticity of an annular bundle of 2 to 8 turns of a cylindrical bristle of poly(ethylene terephthalate). In describing the support the individual bristles may either be interwoven, or merely arranged in a side by side relationship.

The extremities of the individual bristles are joined together to prevent the ends from sticking out through the outer cloth sheath by welding, gluing or ligature. It is thus apparent that the overall ring prosthesis will have a single flexibility. This flexibility will be dependent upon the flexibility of the individual bristles, and/or the number of these individual bristles used to construct the support.

While the device taught and disclosed in Carpentier '861 attempts to achieve flexibility in all planes, the resulting device may have a frame member either rigid or equivalent to the discussed completely flexible ring prosthesis, in either case such a ring prosthesis would have the disadvantages associated with such types of ring prostheses.

Furthermore, a ring prosthesis designed in accordance with Carpentier would suffer disadvantages from the excessive wear of the bristles rubbing against each other. This wear would cause flexural fatigue of the structure during normal activity of the valve. The ring prosthesis could also suffer from fatigue due to the differential application of the stress forces applied to the separate bristles or bristle windings. That is, during the natural movement of the valve the normal stress applied to the ring prosthesis would not be equally applied to each of the bristle strands or windings. This could result is fatigue of some of the bristle strands or windings severely affecting the functioning of the ring prosthesis.

It would thus be desirable to provide a ring prothesis which provides for a more natural flexibility of the valve annulus without suffering the above discussed disadvantages.

DESCRIPTION OF THE DRAWINGS

The present invention may be better understood and the advantages will become apparent to those skilled in the art by reference to the accompanying drawings, wherein like reference numerals refer to like elements in the several figures, and wherein:

FIG. 3 is a end view of the prosthesis of FIG. 1;

FIG. 4 is a partially cut-away top view of a annuloplasty ring prosthesis in accordance with another embodiment of the invention;

FIG. 5 is a partially section side view of the ring prosthesis of FIG. 4;

FIG. 6 is a sectional view of the ring prosthesis of FIG. 4 taken along line 6—6;

FIG. 7 is a sectional view of the ring prosthesis of FIG. 4 taken along line 7—7;

SUMMARY OF THE INVENTION

Figure 1:
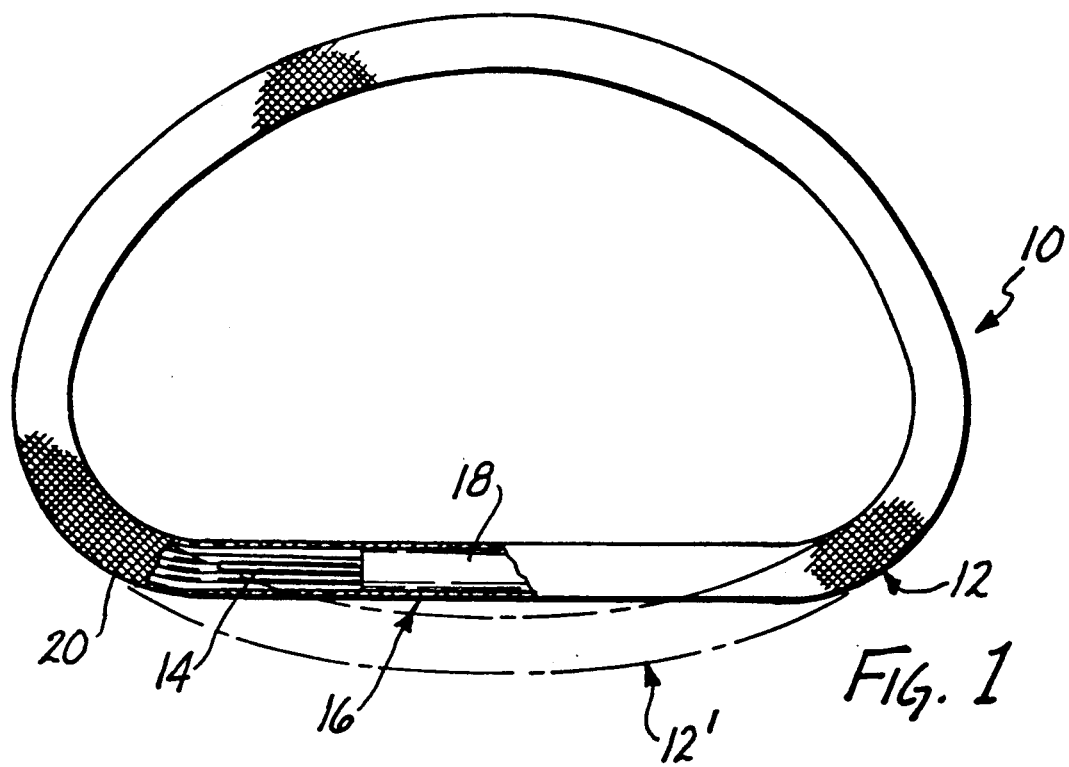
FIG. 1 is a top view of a partially cut-away annuloplasty ring prosthesis in accordance with an embodiment of the invention.

The present invention overcomes the above discussed disadvantages by providing an annuloplasty ring prosthesis which is includes a substantially annular shaped body element with at least a first defined length about its circumference which is substantially more rigid than the remainder of the elements circumference, with the remainder of the body element gradually increasing in flexibility in a direction away from this rigid length. This body element is formed from a non-corrosive, anti-magnetic material, and is wrapped in a material through which sutures can be drawn to suture the prosthesis to the heart valve annulus.

Preferably the annuloplasty ring prosthesis of the invention is dimensioned to be longer in a longitudinal direction than in a lateral direction, with the overall flexibility of the ring being greater in the lateral direction. In another preferred embodiment, the annuloplasty ring prosthesis is formed in the horizontal orientation, with a substantially straight length along one of the longitudinal oriented sides. The substantially more rigid length lies along this straight portion of the ring prosthesis.

In a still further preferred embodiment, the selective flexibility of the ring prosthesis is orientated to provide that a ratio of the stiffness of the ring in the longitudinal direction over the stiffness in the lateral direction is from about 1.15 to about 2.77. The stiffness is calculated by measuring the spring rates of the ring in both directions.

The body element of the ring prosthesis may be formed from individual wire strands bundled together. The discrete rigid portion may be formed by crimping together a length of the wire bundle. In one preferred embodiment the body element is formed from a multi-lumen tubular enclosure and individual non-corrosive, anti-magnetic wire strands positioned individually in each of said tubular enclosure lumens.

In a still further embodiment the body element is formed as a multi-layered structure of one or more individual substantially flat bands of a non-corrosive, anti-magnetic material. The discrete rigid portion of this embodiment can be formed by crimping or spot welding a length of the layers together. This embodiment may be further modified by positioning plastic or other type of elastomer material between the bands, to prevent wear.

The ring prosthesis of the invention is thus formed with a selective flexibility about its circumference while providing a defined structure. That is, the circumference of the prosthesis is defined by the selectively flexible body element which gradually increases in flexibility away from at least one length which is substantially more rigid than the remainder of the body element. The body element allows the surgeon to correct the dilation and reshape the valve, without sacrificing the desired flexibility needed to allow the valve to more naturally open and close. The selectively flexible body element also ensures that the prosthesis will retain its shape as it is being sutured to the valve annulus to reduce the potential of forming multiple plications.

DESCRIPTION OF THE PREFERRED EMBODIMENTS

The present invention is directed to annuloplasty ring prostheses which are sutured to the annulus of a dilated and/or deformed heart valve. The dilation and/or deformation of heart valves may be the result of a disease, natural defect or physical damage to the valve annulus. This dilated and/or deformed heart valve will not completely close, allowing for regurgitation of blood with a closed valve.

The annuloplasty ring prosthesis of the invention is surgically sutured to the valve annulus. This prosthesis restricts the circumference of the dilated valve to a more natural dimension, and also provides sufficient rigidity to reshape the valve. The prosthesis of the invention thus restrains dilation of the valve and allows the surgeon to reshape the valve. The prosthesis of the invention accomplishes these tasks by being designed with selective flexibility about its circumference. The body element is formed about its circumference with at least one defined length which is rigid, with the body element gradually increasing in flexibility is a direction away from this rigid length. By properly suturing the rigid and flexible portions of the prosthesis about the valve annulus, the valve functions in a more normal manner than possible with presently available annuloplasty ring prosthesis.

Figure 2:
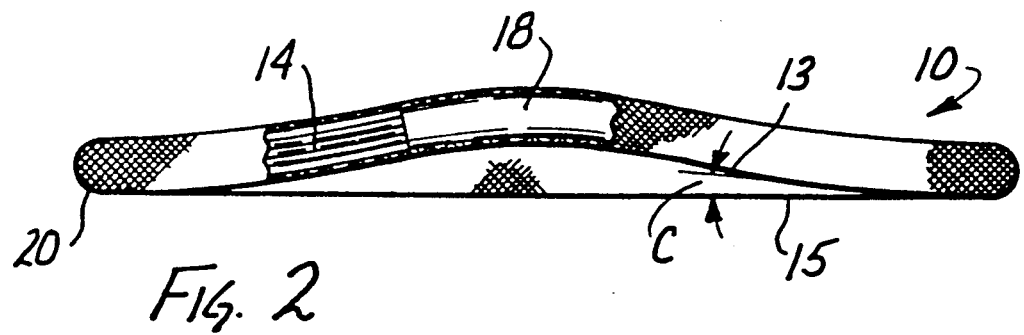
FIG. 2 is a partially cut-away side view of the ring prosthesis of FIG. 1.

Referring now to FIGS. 1 and 2, an annuloplasty ring prosthesis in accordance with an embodiment of the invention is seen generally at 10. Ring prosthesis 10 is formed from a selectively flexible body element, which will be described in greater detail below as being formed from a plurality of individual wire strands 14. This body element has a generally oblong or oval shape. The precise dimensions of ring prosthesis 10, as defined by the body element, is dependent upon whether the ring prosthesis is to implanted about a tricuspid or mitral valve. In any event, the dimensions of ring prosthesis 10 may be designed for any type of valve annulus. Normally, various sized and dimensioned ring prothesis will be available.

As stated, ring prosthesis 10 is constructed from a plurality of individual wire strands, one of which is seen generally at 14. These strands 14 are manipulated to provide the prosthesis with any desired shape. The respective ends, not shown, of each of the wire strands 14 are placed in a generally abutting relationship. The wire ends are then held in position by any suitable manner, e.g. crimping.

The illustrated ring prosthesis 10 is designed for suturing about a mitral heart valve. Prosthesis 10 has the shape generally resembling the letter "D". That is, the illustrated ring prosthesis 10 is designed with a generally oblong shape, with one of the longitudinally oriented sides, seen as side 12, being substantially straight. For the purpose of this discussion the description of the substantially straight side 12 shall mean being substantially straight as seen in a direction illustrated in FIG. 1. Generally, this substantially straight side 12 comprises from about 1/5 to about ⅓ of the total circumference of the ring prosthesis 10.

In accordance with the invention, selectively flexible body element of the ring prosthesis 10 is designed with at least one defined length or portion about its circumference which is substantially more rigid or stiff than the remainder of the ring prosthesis, this rigid length is generally indicated at 16. The flexibility of the ring gradually increases in a direction away from this rigid length 16 to provide the overall prosthesis with a selective flexibility. Generally the rigid length comprises from about ⅛ to ½ of the ring prosthesis circumference. When suturing the ring prosthesis to the valve annulus, this rigid length is positioned adjacent to the anterior cusp of the mitral valve, or the median cusp of the tricuspid valve.

Preferably, the rigid length 16 is defined along the substantially straight side 12. Generally, the rigid length 16 comprises from about ⅜ to about 3/2 of the straight side 12. Thus this straight side 12 will be sutured adjacent to the anterior cusp of a mitral heart valve, or the median cusp of the tricuspid heart valve.

As seen, a malleable tube 18 is fixed about the bundle of wire strands 14 at a location around these abutting ends. This malleable tube 18 is pinched or crimped down upon the bundle of wire strands 14. The malleable tube 18 functions not only to hold the ends of the wire strands 14 in place, but in this embodiment also defines the rigid length 16 of the ring prosthesis 10. The rigid length 16 may comprise less or more than the entire length of the malleable tube 18. If the rigid length 16 comprises more than the length of the tube 18, then the wire strands 14 are pinched, crimped or welded together for this greater length.

It should be noted that the use of the malleable tube 18 simplifies the forming of the rigid length 16. The abutting ends of the wire strands 14 may be fixed together by an adhesive or by welding, with the rigid length 16 formed by selectively welding or in some other manner fixing the individual wire strands 14 together.

Both the wire strands 14, and the malleable tube 18 are formed from a biocompatible material. This material should also be anti-magnetic. One particular suitable material is a cobalt-nickel alloy manufactured under the trademark ELGILOY by the Elgiloy Company, a division of American Gage & Machine Company, 1565 Fleetwood, Elgin, Illinois. This material is also described in U.S. Pat. No. 2,524,661.

Generally, ring prothesis 10 will vary in size from 24 millimeters (mm) to 38 mm. The number of wire strands 14 used to construct the ring prosthesis 10 is dependent upon the desired flexibility, which is dependent upon the diameter of the wire strands 14, and the material from which the strands 14 are made. Generally, the individual wire strands 14 will have an outer diameter of from about 0.008 inch to about 0.022 inch. The number of wire strands 14 used to construct the ring prosthesis 10 will vary from about one to about twelve.

As stated the ring prosthesis of the invention possesses a selective flexibility about its circumference. This selective flexibility is dependent upon many variables, e.g. the composition, outer diameter and size of the individual wire strands 14, and the size of the rigid length 16. Generally, by altering these variables the flexibility of the ring prosthesis is selected to position rigid lengths at locations which provide the needed support to the valve annulus and allow the surgeon to reshape a deformed valve.

In accordance with a preferred embodiment of the invention these variable are manipulated to provide that the ring prosthesis will be stiffer in the longitudinal direction. The longitudinal direction for the ring prosthesis is the longest length, seen generally along line A—A, in FIG. 1. The prosthesis 10 also includes a lateral direction, which is generally the width of the ring prosthesis 10 seen along line B—B. In a further preferred embodiment, the ring prosthesis 10 is designed to provide a ratio of the stiffness of the prosthesis 10 in the longitudinal direction over the stiffness in the lateral direction from about 1.15 to about 2.77.

For the purpose of describing the invention, the stiffness of the ring prothesis 10 in the longitudinal and lateral directions is calculated by determining the spring rate of the ring prothesis 10 for these directions. The spring rate may be calculated by the concept known as Finite Element Analysis. The Finite Element Analysis allows for calculating the spring rate in the longitudinal and lateral directions using the diameter and length of the individual and bundle of wire strands 14, and the rigid length 16. The type of material from which the wire strands 14 and the malleable tube 18 are made is also used in this calculation. For a more detailed discussion of this concept see, "Concept and Applications of Finite Element Analysis", Second Edition, Robert D. Cook, Department of Engineering Mechanics, University of Wisconsin-Madison, John Wiley & Sons, 1981. The shorter the length of the wire strands 14, and thus the smaller the circumference of the prosthesis, the greater the stiffness. For example, a ring prosthesis of 26 millimeters would have a ring spring rate of 160 grams per millimeter, while a ring prosthesis of 38 millimeters would have a ring spring rate of 240 grams per millimeter.

The ring prosthesis 10 further includes an outer sheath 20. This outer sheath 20 fits snugly wrapped about the wire strands 14. This sheath 20 may be any suitable type of biocompatible material, for example a knit fabric such as Dacron polymer (polyethylene terephthalate) fabric.

Preferably, the wire strands are embedded in an elastomeric material, or coated with an elastomeric material or polytetrafluoroethylene to reduce friction between the individual wire strands 14, and thus minimize wear.

In a preferred embodiment, the substantially straight side 12 of the ring prosthesis bows outward from a plane in which lies the remainder of the ring prosthesis 10. This preferred embodiment is seen better in FIG. 2. Generally, the outward curvature of the straight side 12 provides an angle between a line drawn along the side 12, seen generally at 13, and that plane in which lies the remainder of the ring prosthesis 10, seen at 15, of from about 0° to about 15°. This curvature is preferably designed to conform to the geometry of that portion of the mitral valve annulus adjacent to the aortic valve root, and provides for a more compatible fit of the annuloplasty ring prothesis 10 about the mitral valve.

In another still further embodiment of the invention, the side 12 is not substantially straight, but is formed with a slight outward curvature as seen in phantom at side 12'.

While the ring prothesis described and illustrated in FIGS. 1 through 3 provides an improvement over presently available ring prothesis, other more preferable embodiments will now be described. These embodiments provide for a greater degree of control in the flexing of the prosthesis during the normal opening and closing of the associated heart valve, also ensure that the load applied to the prosthesis is evenly applied to the prosthesis structure. The individual wire strands 14 of the previously described embodiment, as illustrated in FIGS. 1-3, are free to move with respect to each other. This movement allows the wire strands 14 to rub against each other which causes unwanted wear. Also, the load applied to the ring prosthesis 10, as the valve opens and closes, unevenly varies between the individual strands 14. This may result in the concentration of the applied load onto one or more of the wire strands 14, which may also result in stress fatigue of those strands 14.

One preferred prosthesis is illustrated in FIGS. 3 through 5 at 22. In this embodiment the selectively flexible body element comprises a multi-lumen elastomeric tube 28, with individual wire strands 24 fitted in respective ones of the individual lumens 26. The positioning of the wire strands 24 in the associated lumens 26 restricts the movement of the strands 24 with respect to each other. This ensures that the load will be borne evenly by the individual strands 24. Furthermore, the individual wire stands 24 can not rub against each other. This reduces the wearing of the strands 24.

The number of individual wire strands 24 used to construct this embodiment is dependent upon flexibility desired for the prosthesis 22. Generally, from about 2 to about 9 individual strands 24 are used to construct the prosthesis 22, with the individual strands 24 having similar dimensions and prepared from a similar material to that used for the wire strands 14 of the previously described embodiment.

The prosthesis 22 is also designed to have selective flexibility. This selective flexibility is provided by forming about the circumference of the prosthesis 22 one or more defined lengths, one or which is seen generally at 30, which are substantially more rigid than the remainder of the prosthesis 22 circumference. The prosthesis 22 is designed so that the flexibility of the prosthesis increases in a direction away from these lengths 30. The rigid lengths 30 of the prosthesis 22 may be formed by any suitable method, such as those methods described above for the rigid length 16 of the previous embodiment.

In the illustrated embodiment, the multi-lumen elastomeric tubing 28, as seen in FIG. 4, does not run the entire circumference of the ring prosthesis 22. A portion of this elastomeric tubing 28 is removed, or the length of such tubing 28 is provided to expose a portion of the wire strands 24, preferably at a location adjacent to the position at which the wire strands 24 abut. The abutting ends of the wire strands 24 are held together by any suitable manner. A malleable tube 32 is secured about the wire strands 24 at this exposed location in a manner as described above. The crimping, pinching or welding of the tube 32 defines the rigid length 30. As with the previous embodiment, the size of the rigid length 30 is determined by the extend to which the tube 32, and adjacent portions of the wire strands 24 are crimped, pinched or welded. The arrangement of the individual wire strands 24 in the associated lumens 26 is seen better in FIG. 6, while the placement of the wire strands 24 in the malleable tube 32 is best seen in FIG. 7.

A preferred embodiment, as illustrated, provides that the ring prosthesis 22 is also designed with a substantially straight side, seen generally at 34. This straight side 34 is similar to the straight side 16 as described above for the previous embodiment, and will not be described in any greater detail herein. Furthermore, this straight side 34 may be curved outward in a manner similar to side 16 or the previously described embodiment, with this side 34 also preferably being formed outwardly curving as seen at 34'.

Referring now to FIGS. 8 through 11 a more preferred ring prosthesis of the invention, seen generally at 36, will be described. In this embodiment the selectively flexible body element of the annuloplasty ring prothesis 36 is defined by a spiral wire band structure. The individual spiral layers are formed by selectively wrapping a single band to form the spiral structure, or by layering individual bands upon one another, with one of such bands being seen at 38. Preferably a plurality of individual bands 38 are layered upon one another to form the multi-layered structure. The ring prosthesis 36 may include from one to about 6 of these spiral layers. These bands 38 are formed from a biocompatible, anti-magnetic material.

Figure 10:
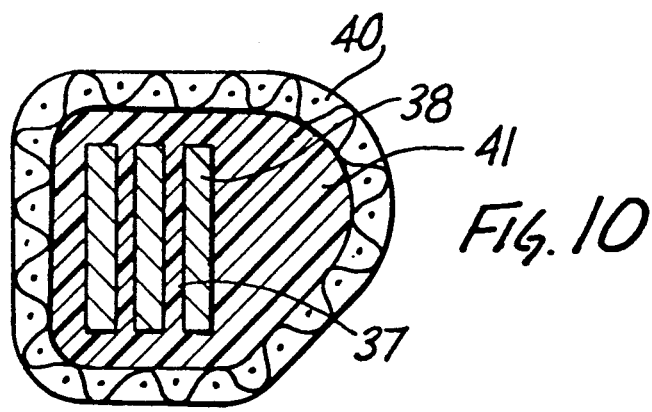
FIG. 10 is a cross-sectional view of the prosthesis of FIG. 8 along lines 10—10.
Figure 8:
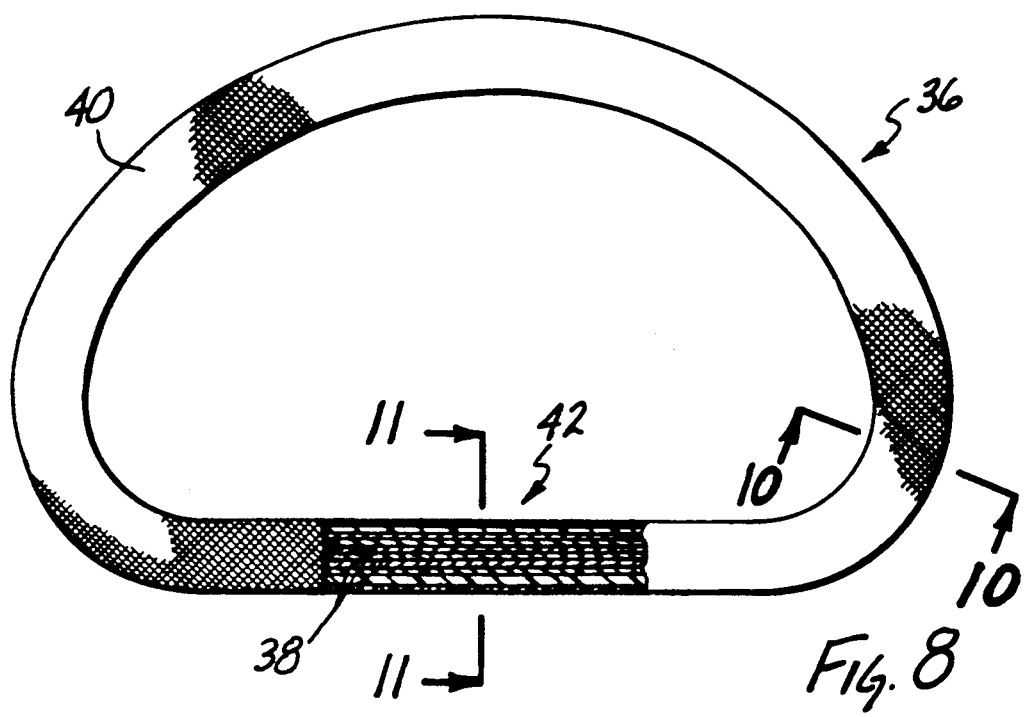
FIG. 8 is a top view of a partially cut-away annuloplasty ring prosthesis in accordance with a still further embodiment of the invention.
Figure 9:
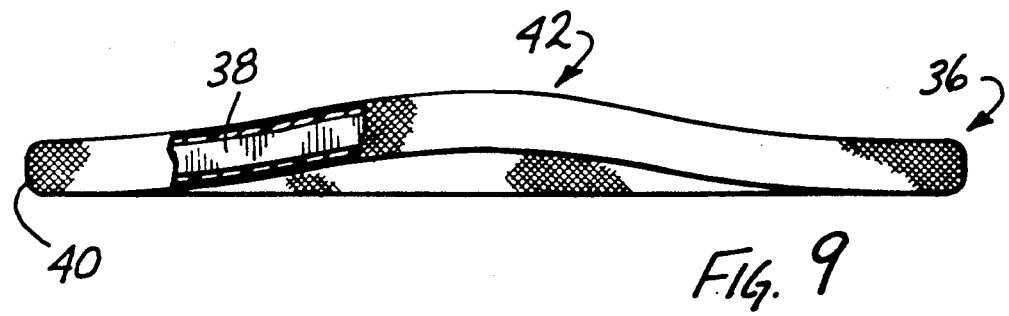
FIG. 9 is a partially sectioned side view of the ring prosthesis of FIG. 8.
Figure 11:
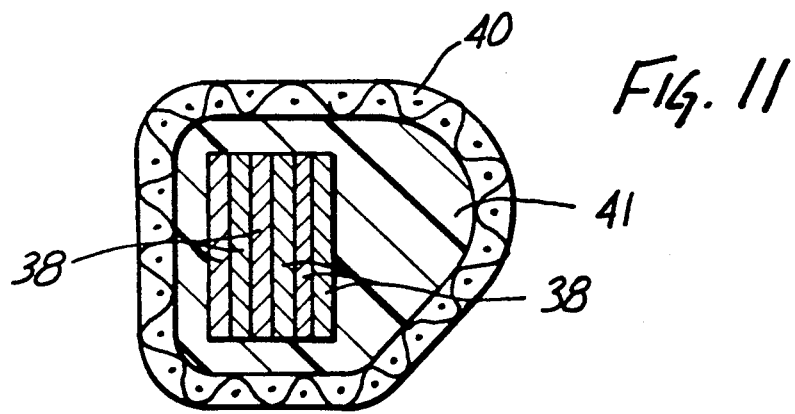
FIG. 11 is a cross-sectional view of the prosthesis of FIG. 8 along lines 11—11.

This spiral structure is held within a cloth sheath 40 in a manner similar to the previously described embodiments. Preferably, in order to reduce friction between adjacently positioned bands, an elastomeric material is placed between the individual spiral layers, e.g. the individual bands 38, with such material seen at 37 in FIG. 10. The elastomeric material 37 also surrounds the outside of the bands 38. As seen in FIGS. 10 and 11, the cloth sheath 40 bulges outwards along one side, with this bulge, as seen at 41, filled with the elastomeric material 37. This bulge 41 is preferentially positioned along the outside of the prosthesis 36. Sutures will be passed through the bulge 41.

The selectively flexible body element, as defined by the spiral band 38 structure is also formed about its circumference with one or more defined lengths, one of which is seen generally at 42, which are substantially more rigid than the remainder of the body element circumference. This aspect of prosthesis 36 is similar to the previously discussed embodiments, and will not be described great detail herein. The rigid length 42 is typically formed by crimping or spot welding the individual bands 38 together for the desired length.

As seen in FIG. 11, none of the elastomeric material 37 is positioned between the bands 38 along the rigid length 42. This occurs because the individual bands 38 are overlapped at this location. That is the respective ends, not shown, of each band 38 are overlapped. Preferably the respective ends are tapered. This better distributes the stresses exerted upon the prosthesis 36 than if the respective ends were merely squared off.

The desired size of this rigid length 42 is also similar to that of the above described embodiments. Generally, this rigid length 42 is from about ⅛ to about ½ of the ring prosthesis 36 circumference. The flexibility of the body element also varies in a direction away from this rigid length 42 in a manner similar to that described for the previous embodiments. That is, preferably a ratio of the stiffness of the body element, as defined by the spiraled bands 38 in the longitudinal direction over the stiffness in the lateral direction is from about 1.15 to about 2.77.

The use of a spiraled structure prepared by the overlaying of one or more bands 38 ensures that the force applied against the prosthesis 36 is better distributed over the various layers of the bands 38. That is, the application of force against the prothesis 36 is better distributed to the various band 38, than is distributed to the individual wire strands 24, in the embodiment of FIGS. 4–7, or strands 14, in the embodiment of FIGS. 1–3. The result is a more even application of load to the entire ring prosthesis 36 in both the longitudinal and lateral directions.

The precise number of spiral windings forming the body element is dependent upon the materials used for the bands 38, as well as the thickness of the individual band 38 layers forming the multi-layered structure.

Generally, from about 1 to about 6 spiral layers or individual bands 38 are used, while the thickness of each layer or band 38 may be from about 0.002 to about 0.008 of an inch.

While the preferred embodiments have been described, various modifications and substitutions may be made thereto without departing from the scope of the invention. Accordingly, it is to be understood that the invention has been described by way of illustration and not limitation.

What is claimed is:

1. An annuloplasty ring prosthesis for suturing about a hear valve annulus comprising:
   a selectively flexible body member which is formed with a substantially annular shape proportioned to fit about the circumference of said heart valve annulus, said selectively flexible body member having at least one defined length which is substantially more rigid than the remainder of said selectively flexible body member, said substantially more rigid defined length comprising a portion of said member which curves upward out of a plane in which the remainder of said body member substantially lies; and
   a covering surrounding said body member which is formed to permit the passage of sutures.

2. The annuloplasty ring prosthesis of claim 1 wherein said rigid length defines from about ⅛ to about ½ of the circumference of said selectively flexible body member.

3. The annuloplasty ring prosthesis of claim 1 wherein said body member is configured with two opposing longitudinal sides and two opposing lateral sides, with said longitudinal sides being longer than said lateral sides and said rigid length being defined along one of said longitudinal sides.

4. The annuloplasty ring prosthesis of claim 3 wherein said one of said longitudinal sides is defined by from about 1/5 to about ⅓ of the circumference of said member.

5. The annuloplasty ring prosthesis of claim 4 wherein said rigid length is defined by from about ⅛ to about 3/2 of said longitudinal side.

6. The annuloplasty ring prosthesis of claim 5 wherein said selectively flexible body member has varying degrees of stiffness as defined by a ratio of stiffness, as measured by the spring rate of said prosthesis in the longitudinal direction over the spring rate of said prosthesis in the lateral direction of from about 1.15 to about 2.77.

7. The annuloplasty ring prosthesis of claim 3 wherein said selectively flexible body member has varying degrees of stiffness as defined by a ratio of stiffness, as measured by the spring rate of said prosthesis in the longitudinal direction over the spring rate of said prosthesis in the lateral direction of from about 1.15 to about 2.77.

8. The annuloplasty ring prosthesis of claim 7 wherein said member gradually increases in flexibility about its circumference in a direction away from said defined rigid length.

9. An annuloplasty ring prosthesis for suturing about a heart valve annulus comprising:
   a selectively flexible body member which is formed with a substantially annular shape proportioned to fit about the circumference of said heart valve annulus, said flexible body member being formed from one or more individual substantially flat bands wrapped upon one another to form a multi-layered structure, said selectively flexible body member being at least one defined length which is substantially more rigid than the remainder of said body member, said defined length defined by a portion of said body member which curves upward out of a plane in which the remainder of said body member substantially lies; and
   a covering surrounding said body member which is formed to permit the passage of sutures.

10. The annuloplasty ring prosthesis of claim 9 wherein said defined rigid length is defined by from about ⅛ to about ½ of the circumference of said member.

11. The annuloplasty ring prosthesis of claim 9 wherein said body member is configured with two opposing longitudinal and two opposing lateral sides, with the longitudinal sides being longer than the lateral sides and with said rigid length be defined by portion of one of said longitudinal sides.

12. The annuloplasty ring prosthesis of claim 9 wherein said defined rigid length, is defined by at least a part of one of said longitudinal sides, which side curves outward from said plane.

13. The annuloplasty ring prosthesis of claim 12 wherein said one of said longitudinal sides is defined by from about 1/5 to about ⅓ of the circumference of said member.

14. The annuloplasty ring prosthesis of claim 13 wherein said defined rigid length is defined by from about ⅛ to about 3/2 of said longitudinal side.

15. The annuloplasty ring prosthesis of claim 14 wherein said selectively flexible body member has varying degrees of stiffness as defined by a ratio of stiffness, as measured by the spring rate of said prosthesis in the longitudinal direction over the spring rate of said prosthesis in the lateral direction of from about 1.15 to about 2.77.

16. The annuloplasty ring prosthesis of claim 15 wherein said body member is a single wound band.

17. The annuloplasty ring prosthesis of claim 16 wherein said defined rigid length is formed by crimping or welding together a length of said individual band.

18. The annuloplasty ring prosthesis of claim 15 wherein said body member is a plurality of individual bands.

19. The annuloplasty ring prosthesis of claim 18 wherein said defined rigid length is formed by crimping or welding together a length of said individual bands.

20. The annuloplasty ring prosthesis of claim 18 wherein said member gradually increases in flexibility about its circumference in a direction away from said defined rigid length.

21. The annuloplasty ring prosthesis of claim 11 wherein said selectively flexible body member has varying degrees of stiffness as defined by a ratio of stiffness, as measured by the spring rate of said prosthesis in the longitudinal direction over the spring rate of said prosthesis in the lateral direction of from about 1.15 to about 2.77.

22. The annuloplasty ring prosthesis of claim 11 wherein said member gradually increases in flexibility about it circumference in a direction away from said defined rigid length.

23. The annuloplasty ring prosthesis of claim 9 wherein said member gradually increases in flexibility about its circumference in a direction away from said defined rigid length.

24. An annuloplasty ring prosthesis for suturing about a heart valve annulus comprising:
- a selectively flexible body member formed from a plurality of individual wire strands arranged in a bundle and in a substantially annular shape proportioned to fit about the circumference of said heart valve annulus, said selectively flexible body member having at least one length which is substantially more rigid than the remainder of said selectively flexible body member as defined by fixing together said individual wire strands along said length, wherein said bundle of individual wire strands is arranged in an elastomeric tube, with the individual strands embedded in an elastomeric material held within said tube; and
- a covering surrounding said selectively flexible body member which is formed to permit the passage of sutures.

25. The annuloplasty ring prosthesis of claim 24 wherein said defined rigid length is defined by from about ⅛ to about ½ of the circumference of said selectively flexible body.

26. The annuloplasty ring prosthesis of claim 24 wherein said body member is configured with two opposing longitudinal sides and two opposing lateral sides, with said longitudinal sides being longer than said lateral sides, and said rigid length being defined along one of said longitudinal sides.

27. The annuloplasty ring prosthesis of claim 26 wherein one of said longitudinal sides is substantially straight, and wherein said rigid length is defined by at least a part of said substantially straight longitudinal side.

28. The annuloplasty ring prosthesis of claim 27 wherein said rigid length is defined by from about ⅜ to about 3/2 of said straight longitudinal side.

29. An annuloplasty ring prosthesis for suturing about a heart valve annulus comprising:
- a selectively flexible body member formed from a plurality of individual wire strands arranged in a bundle and in a substantially annular shape proportioned to fit about the circumference of said heart valve annulus, said selectively flexible body member having at least one length which is substantially more rigid than the remainder of said selectively flexible body member as defined by fixing together said individual wire strands along said length, wherein each of said individual wire strands is coated with polytetrafluoroethylene or an elastomeric material; and
- a covering surrounding said selectively flexible body member which is formed to permit the passage of sutures.

30. The annuloplasty ring prosthesis of claim 1 wherein said defined rigid length is defined by from about ⅛ to about ½ of the circumference of said selectively flexible body member.

31. The annuloplasty ring prosthesis of claim 1 wherein said body member is configured with two opposing longitudinal sides and two opposing lateral sides with said longitudinal sides being longer than said lateral sides and said rigid length being defined along one of said longitudinal sides.

32. The annuloplasty ring prosthesis of claim 31 wherein said one of said longitudinal sides is substantially straight.

33. The annuloplasty ring prosthesis of claim 32 wherein said selectively flexible body member has varying degrees of stiffness as defined by a ratio of stiffness, as measured by the spring rate of said sides in said longitudinal direction over the spring rate of said sides in said lateral direction of from about 1.15 to about 2.77.

34. The annuloplasty ring prosthesis of claim 29 wherein said body member is configured with a substantially straight side, said substantially straight side being defined by from about 1/5 to about ⅓ of the circumference of said member.

35. The annuloplasty ring prosthesis of claim 34 wherein said rigid length is defined by from about ⅜ to about 3/2 of said straight longitudinal side.

36. The annuloplasty ring prosthesis of claim 31 wherein said selectively flexible body member has varying degrees of stiffness as defined by a ratio of stiffness, as measured by the spring rate of said sides in said longitudinal direction over the spring rate of said sides in said lateral direction of from about 1.15 to about 2.77.

37. The annuloplasty ring prosthesis of claim 35 wherein said selectively flexible body member has varying degrees of stiffness as defined by a ratio of stiffness, as measured by the spring rate of said sides in said longitudinal direction over the spring rate of said sides in said lateral direction of from about 1.15 to about 2.77.

38. The annuloplasty ring prosthesis of claim 29 wherein said member gradually increases in flexibility about its circumference in a direction away from said defined rigid length.

39. An annuloplasty ring prosthesis for suturing about a heart valve annulus comprising:
- a selectively flexible body member having a substantially annular shape proportional to fit about the circumference of said heart valve annulus which is formed from a multi-lumen tubular enclosure, with individual wire strands positioned individually in each of said tubular enclosure lumens, said body member being formed at one or more positions about its circumference with defined lengths which are substantially more rigid than the remainder of said body circumference, said member gradually increasing in flexibility about its circumference in a direction away from each of said defined rigid lengths; and
- means associated with said body member for enclosing said tubular structure, which is formed to permit suturing of said ring prosthesis about said heart valve.

40. The annuloplasty ring prosthesis of claim 39 wherein said prosthesis member includes only one of said defined rigid lengths, which is defined by from about ⅛ to about ½ of the circumference of said member.

41. The annuloplasty ring prosthesis of claim 39 wherein said body member is dimensioned to be longer in a longitudinal direction than in a lateral direction, with said member being stiffer in said longitudinal direction.

42. The annuloplasty ring prosthesis of claim 41 wherein a portion of one side of said body member along said longitudinal direction is substantially straight, and wherein said prosthesis member includes only one of said defined rigid lengths, with said defined rigid length being defined by at least a part of said straight side.

43. The annuloplasty ring prosthesis of claim 42 wherein said straight side is defined by the from about 1/5 to about ⅓ of the circumference of said member.

44. The annuloplasty ring prosthesis of claim 43 wherein said defined rigid length is defined by from about ⅓ to about 3/2 of said straight side.

45. The annuloplasty ring prosthesis of claim 44 wherein said selectively flexible body member has varying degrees of stiffness as defined by a ratio of stiffness, as measured by the spring rate of said prosthesis in the longitudinal direction over the spring rate of said prosthesis in the lateral direction of from about 1.15 to about 2.77.

46. The annuloplasty ring prosthesis of claim 45 wherein said defined rigid length is formed by positioning a malleable material around a portion of said body member which is to define said rigid length, and pinching said material down upon said body.

47. The annuloplasty ring prosthesis of claim 46 wherein said malleable material is pinched down upon said body member after a portion of said multi-lumen tube is removed to expose said wire strands.

48. The annuloplasty ring prosthesis of claim 42 wherein said selectively flexible body member has varying degrees of stiffness as defined by a ratio of stiffness, as measured by the spring rate of said prosthesis in the longitudinal direction over the spring rate of said prosthesis in the lateral direction of from about 1.15 to about 2.77.

49. The annuloplasty ring prosthesis of claim 41 wherein said selectively flexible body member has varying degrees of stiffness as defined by a ratio of stiffness, as measured by the spring rate of said prosthesis in the longitudinal direction over the spring rate of said prosthesis in the lateral direction of from about 1.15 to about 2.77.

* * * * *

REEXAMINATION CERTIFICATE (3879th)

United States Patent [19]
Lam et al.

[11] B1 5,104,407
[45] Certificate Issued Sep. 21, 1999

[54] SELECTIVELY FLEXIBLE ANNULOPLASTY RING

[75] Inventors: Hung L. Lam, Norco; Than Nguyen, Huntington Beach, both of Calif.; Alain Carpentier, Paris, France

[73] Assignee: Baxter International Inc., Deerfield, Ill.

Reexamination Request:
No. 90/004,913, Feb. 9, 1998

Reexamination Certificate for:
Patent No.: 5,104,407
Issued: Apr. 14, 1992
Appl. No.: 07/587,486
Filed: Sep. 20, 1990

Related U.S. Application Data

[63] Continuation of application No. 07/310,424, Feb. 13, 1989, abandoned.

[51] Int. Cl.$^6$ ........................................ A61F 2/24
[52] U.S. Cl. .................................................. 623/2
[58] Field of Search ..................................... 623/2

[56] References Cited

FOREIGN PATENT DOCUMENTS 577022  10/1977  U.S.S.R. ........................ A61F 1/22

*Primary Examiner*—David J Isabella

[57] ABSTRACT

An annuloplasty ring prosthesis which is formed from a selectively flexible body element having at least one defined length about its circumference which is substantially rigid. The remainder of the body element gradually increases in flexibility. The body element is a substantially annular shaped body element which is designed to be sutured to the annulus of a heart valve. The body element is formed from a non-corrosive, anti-magnetic material, and is wrapped in a material through which sutures can be drawn to suture the prosthesis to the heart valve annulus.

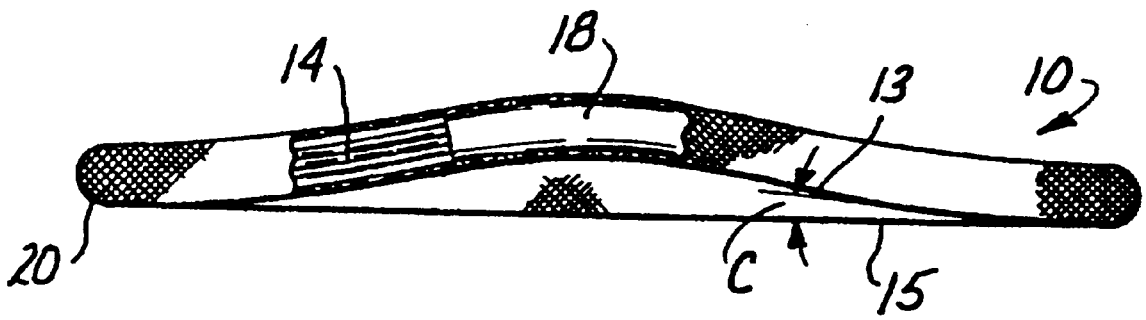

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–49 is confirmed.

* * * * *